United States Patent [19]

Nalepa et al.

[11] 4,373,549
[45] Feb. 15, 1983

[54] MASS FLOW/PRESSURE CONTROL SYSTEM

[75] Inventors: Roger A. Nalepa, Landenberg, Pa.; Michael A. Casale, Newark, Del.

[73] Assignee: Hewlett-Packard Company, Palo Alto, Calif.

[21] Appl. No.: 11,333

[22] Filed: Feb. 12, 1979

[51] Int. Cl.[3] ............................................. F16K 31/02
[52] U.S. Cl. ................................. 137/487.5; 73/702; 137/8; 137/12; 137/557
[58] Field of Search .................. 137/8, 14, 487.5, 557; 73/23.1, 702, 861, 4 R

[56] References Cited

U.S. PATENT DOCUMENTS

| | | | |
|---|---|---|---|
| 3,762,223 | 10/1973 | Feuer et al. | 73/702 |
| 3,842,676 | 10/1974 | Brown et al. | 73/702 X |
| 4,086,804 | 5/1978 | Ruby | 137/487.5 X |

Primary Examiner—William R. Cline
Attorney, Agent, or Firm—Donald N. Timbie

[57] ABSTRACT

An input valve having an input that can be coupled to a source of pressurized gas is open during first portions of successive cycles and closed during the remainder. A volume V is connected between the output of the valve and a load, and gas flows through the volume V to a load during the entire cycle. Pressure in the volume V is measured at the end of the first portion of each cycle and/or at the end of each cycle, and means responsive to a pressure can be used to control the flow of gas through the input valve so as to maintain the pressure on the load at a predetermined value or the difference in the pressures can be used to maintain a constant flow to the load. An output valve can be inserted between the volume and the load and closed while pressure measurements are being made so that the pressure is constant during the measurement. In one embodiment, a reserve volume can be coupled to the output valve and a third valve can be coupled between the reserve volume and the load so as to smooth out variations in pressure on the load. In this last embodiment, the output and third valves are operated out of phase and in such manner that the input valve and output valve are closed when the measurement is taken at the end of a first portion of a cycle, and the input and third valves are shut when the pressure is being measured at the end of a cycle.

17 Claims, 6 Drawing Figures

MASS FLOW/PRESSURE CONTROL SYSTEM

BACKGROUND OF THE INVENTION

In gas chromatographs, as well as other apparatus, it is important to control the flow of gas through a load. Some systems operate in response to means for sensing the mass flow through the load, and others operate in response to the pressure applied to it. Mechanical systems are generally inaccurate, have a low degree of reproducibility, and because they do not employ feedback, they are susceptible to variations in temperature as well as to variations in the pressure of the supply gas. Systems are available that utilize a thermal mass flow sensor as a feedback element in a closed loop system so as to provide accuracy in the presence of temperature variations, but their performance at low flow rates reveals a low degree of reproducibility, and their nonlinearity limits the dynamic range within which they can be used with reasonably good results. Furthermore, it is necessary to change the calibration for each gas because of differences in thermal conductivity and specific heat.

BRIEF DISCUSSION OF THE INVENTION

The sensing apparatus of this invention is easily controlled by electronic means and lends itself to the use of feedback so as to eliminate errors due to temperature drift and variations in supply pressure. It yields linear results over a nearly limitless dynamic range and is especially effective at very low flow rates. No calibration or change is required regardless of the gas involved, and it provides information from which either mass flow or pressure can be controlled without additional expense.

In accordance with the invention, gas is permitted to flow into a given volume from a pressurized source and the pressure in the volume is measured. The gas is then transferred from the volume, either directly or indirectly, to the load and the pressure in the volume is measured once again. By knowing the temperature of the gas and the time between flow into the volume and flow out of it, the mass flow that occurs during that time can be calculated, and because the pressures are known, they can be used as an indication of the pressure on the load.

Although the various embodiments of the invention will be described as they would be used for supplying carrier gas to the column of a chromatograph, it will be understood that any other hydraulic load could be substituted for the column. In the figures of the drawing showing structure, corresponding components are designated by the same numerals; and in the graphs used in explaining the operation, corresponding control waves have the same designations.

Figure 1:
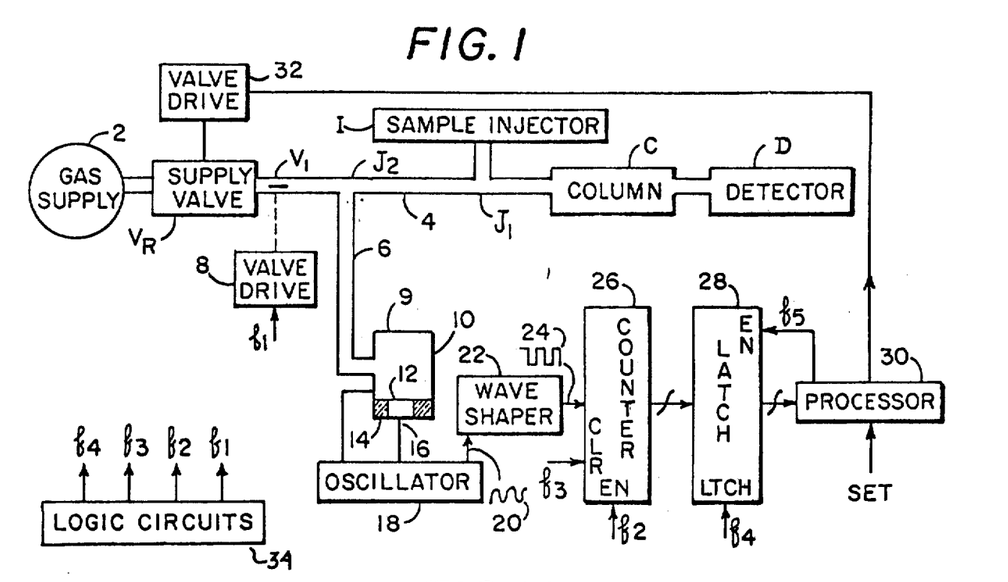
FIG. 1 illustrates apparatus incorporating the invention in which measurements are made of the pressure in a volume while it is changing at the ends of the periods when gas is flowing into and out of the volume.

Turning now to FIG. 1, a pressurized supply 2 of carrier gas is connected to a regulating valve $V_R$, and a tube 4 is connected between the output of the valve $V_R$ and the input to a chromatographic column C. Samples of chemicals to be analyzed are injected by a sample injector 1 into the tube 4 at a junction $J_1$ just ahead of a chromatographic column C, and the output of the column C is coupled to any suitable detector D. A tube 6 is conductively joined to the tube 4 at a junction $J_2$ that is between the valve $V_R$ and the junction $J_1$, and a valve $V_1$ that controls the opening in the tube 4 is mounted in the tube 4 between the regulating valve $V_R$ and the junction $J_2$. The valve $V_1$ is controlled by a valve drive 8 that functions in response to a wave $f_1$. A transducer 9 that converts pressure applied to it into an electrical signal is connected to the tube 6. Although the transducer 9 may be one of many types, it is shown by way of illustration as being comprised of a cylindrical metal tank 10 having a flexible bottom 12 that can move up and down under pressure introduced into the tank via the tube 6. An annular ring 14 of insulating material serves as a spacer between the bottom 12 of the tank 10 and a metal disc 16. Thus, the bottom 12 of the tank 10, the annular ring 14, and the metal disc 16 form a capacitor having a capacitance that varies with the pressure in the tank 10. By electrically coupling the tank 10 and the disc 16 to the tuned circuit of an oscillator 18, fluctuations in the capacitance caused by the pressure vary the frequency of the oscillator. The output of the oscillator 18, which is generally sinusoidal in shape, as indicated by the wave 20, is coupled to a waveshaping circuit 22 that amplifies and clips the output of the oscillator 18 so as to form square waves, as indicated at 24.

The square waves 24 are applied to a counter 26 that is turned on by a wave $f_2$ applied to its "enable" input. While enabled, it counts the number of cycles in the square wave 24 and supplies a corresponding digital number to a latch 28. The latch 28 acquires the digital number at the output of the counter 26 in response to a wave $f_4$ applied to its latch terminal. After this, the counter 26 may be cleared by a wave $f_3$ applied to its clear terminal. The digital output of the latch 28 is conducted to a processor 30 which supplies a wave $f_5$ to the enable terminal of the latch 28 so as to make the digital information stored in it available to the processor 30.

The desired pressure or mass flow is introduced into the processor 30 via a SET input. In a manner to be explained, the processor 30 calculates the difference between either the pressure SET input or the mass flow SET input and the actual values determined from the data provided by the counter 26. The difference is then used in any suitable manner to control the opening in the supply valve $V_R$ by means of a valve drive 32. The various waves $f_1$, $f_2$, $f_3$ and $f_4$ are derived in any suitable manner by logic circuits 34.

Operation of FIG. 1

Figure 1A:
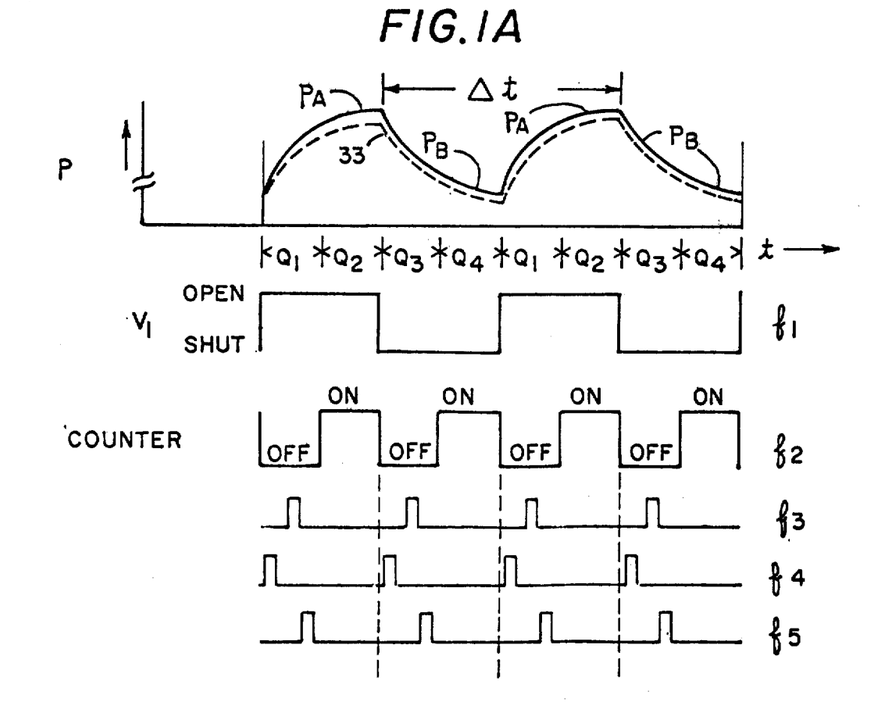
FIG. 1A is a series of graphs used in explaining the operation of FIG. 1.

The pressure in the tank 10 varies in cyclic fashion as indicated by the pressure wave P of FIG. 1A. During the first two quarter-cycles, $Q_1$ and $Q_2$, the valve $V_1$ is open, as indicated by the graph $f_1$. Gas flows from the gas supply 2 through the regulating valve $V_R$, the valve $V_1$ and the tube 4 into the column C and through the tube 6 into the tank 10 of the pressure transducer 9. As the pressure of the supply 2 is greater than any pressure in the system, the pressure in the transducer 9 increases, and the frequency of the output 20 of the oscillator 18 drops. The number of cycles of the square waves 24 occurring during the second quarter $Q_2$ are counted in the counter 26 by activating it during the quarter $Q_2$, as indicated by the waves $f_2$. The digital word representing this count appears at the output of the counter 26 and is stored in the latch 28 shortly thereafter by application of one of the pulses of the wave $f_4$ to the latch terminal. Before the start of the quarter $Q_3$, one of the pulses from the wave $f_3$ is applied to the "clear" input of the counter 26 so that its count goes back to zero. The number of cycles, Ct#1, of the wave 24 counted during a quarter $Q_2$ indicates the average pressure $P_A$ occurring during this time. When the processor 30 is ready to receive the digital word for Ct#1 from the latch 28, it supplies one of the pulses from the wave $f_5$ to the "enable" input. The processor 30 calculates the pressure $P_A$ from Ct#1 by making due allowance for the characteristics of the transducer 9, as will be explained in the description of FIG. 3.

At the end of the second quarter $Q_2$, valve $V_1$ closes, allowing the tank 10, the tube 6 and the portion of the tube 4 between the valve $V_1$ and the column C to discharge gas into the column C. As the discharge proceeds, the pressure drops during quarters $Q_3$ and $Q_4$. During the quarter $Q_4$, the counter 26 is activated and produces a count, Ct#2, indicating the average pressure $P_B$ occurring during $Q_4$. $P_B$ is calculated from Ct#2 by the processor 30 so as to allow for any non-linearity in the transducer 9.

Calculation of Mass Flow

The two pressure measurements $P_A$ and $P_B$ are used by the processor 30 to calculate mass flow $\dot{m}$. The ideal gas law states that $$PV = nRT \quad (1)$$

where P is pressure, V is the volume, n is the number of moles, T is the absolute temperature, and R is the universal gas constant. By taking the derivative and rearranging terms, we obtain $$\frac{dn}{dt} = \frac{dP}{dt} \frac{V}{RT} \quad (2)$$

or $$\frac{\text{flow in moles}}{\text{unit time}} = \frac{P_A - P_B}{\Delta t} \frac{V}{RT} \quad (3)$$

where $\Delta t$ is the duration of one cycle. Since an ideal gas has 22,400 ML per mole at standard pressure and temperature, the result of equation (3) can be converted to a volume flow rate referenced to standard temperature and pressure, as commonly done in gas chromatography. More importantly, because the conversion constant of 22,400 ML per mole is the same for any ideal gas, the sensor shown in FIG. 1 does not need recalibration for different gases.

It is apparent that the processor 30 can be made to calculate the actual mass flow and compare it to the mass flow supplied at the set point so as to derive an error signal that can be applied to the valve drive 32 and set the valve $V_R$ to obtain the desired mass flow. If, however, it is desired to operate with a predetermined pressure at the input of the column C, this can be done by comparing $P_B$, which is very nearly equal to the pressure at the head of the column C, with the desired pressure so as to develop an error signal for controlling the valve $V_R$ through its drive 32. If the mass flow or pressure desired is lowered, the pressure indicated by the transducer 9 may follow the dashed pressure curve 33.

Figure 2:
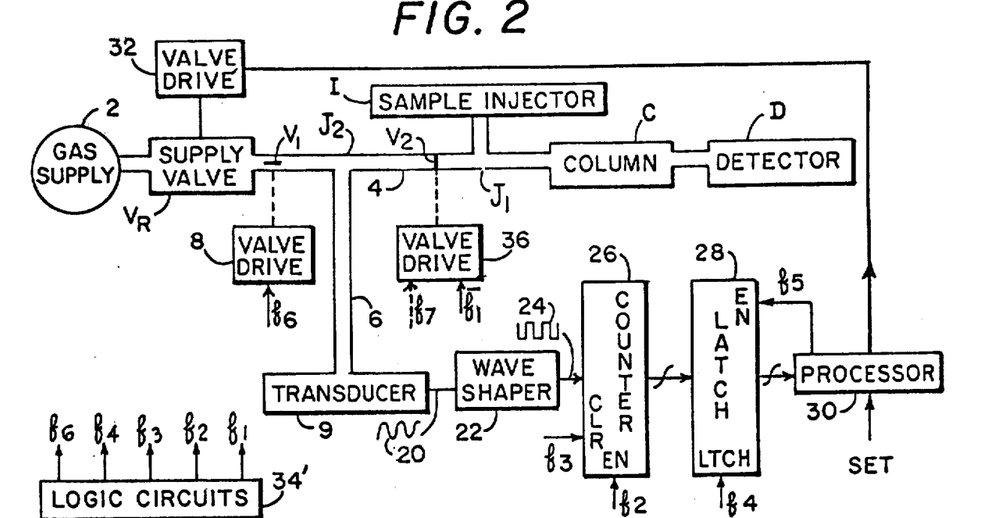
FIG. 2 illustrates apparatus incorporating the invention which can be operated in two modes. In one, the volume is held constant for a time after gas has flowed into it and pressure measurements are made during this time. In the other, the volume is also held constant for a time after gas has flowed out of it and pressure measurements are made during this time.
Figure 2A:
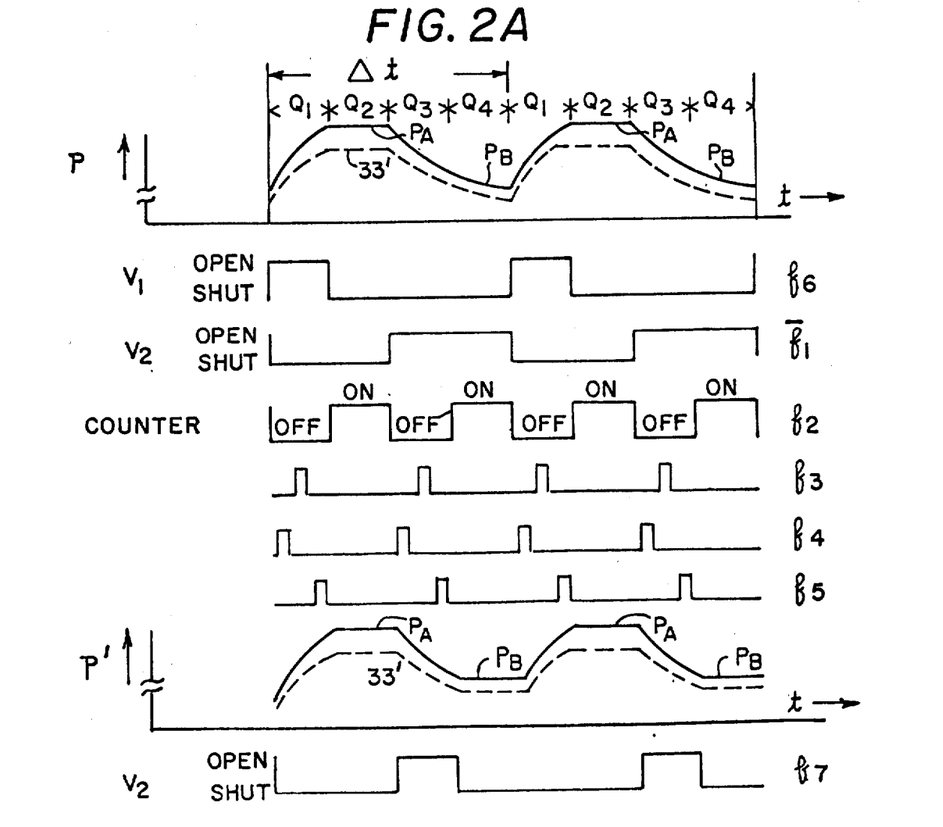
FIG. 2A is a series of graphs used in explaining the operation of FIG. 2.

The apparatus of FIG. 2 is similar to that of FIG. 1 except for the addition of a valve $V_2$ in the tube 4 at a point between $J_2$ and $J_1$, and a valve drive 36. As illustrated, the waves supplied by the logic circuit 34' differ from the waves supplied by the logic circuit 34 of FIG. 1. The drivers 8 and 36 for the valves $V_1$ and $V_2$ are operated as indicated by the graphs $f_6$ and $f_1$ respectively. During the first quarter-cycle $Q_1$, $V_1$ is open and $V_2$ is closed so that gas from the supply 2 enters the transducer 9 but does not flow into the column C. During the second quarter-cycle, $Q_2$, the valve $V_1$ is also closed. This makes the pressure constant during $Q_2$, as indicated at $P_A$ in the graphs P of FIG. 2A. During $Q_2$, the counter 26 is activated as before, as indicated by the graph $f_2$. Because the pressure $P_A$ is constant, a more accurate reading is attained, but the pressure $P_B$ is measured during $Q_3$ when, as in FIG. 1, it is falling. Operation at lower pressures and flow rates is indicated by the dotted curve 33'.

The pressure graphs P' illustrate operation of the apparatus of FIG. 2 so as to improve the accuracy with which the pressure $P_B$ is measured by holding it constant, as indicated in the pressure graphs P'. This is done by keeping the given volume V associated with the transducer P constant during the fourth quarter-cycles $Q_4$. To do this, the valve $V_2$ is controlled by a wave $f_7$, rather than the wave $\bar{f}_1$, so that both valves $V_1$ and $V_2$ are closed during the quarter-cycle $Q_4$.

Preferred Embodiment

Figure 3:
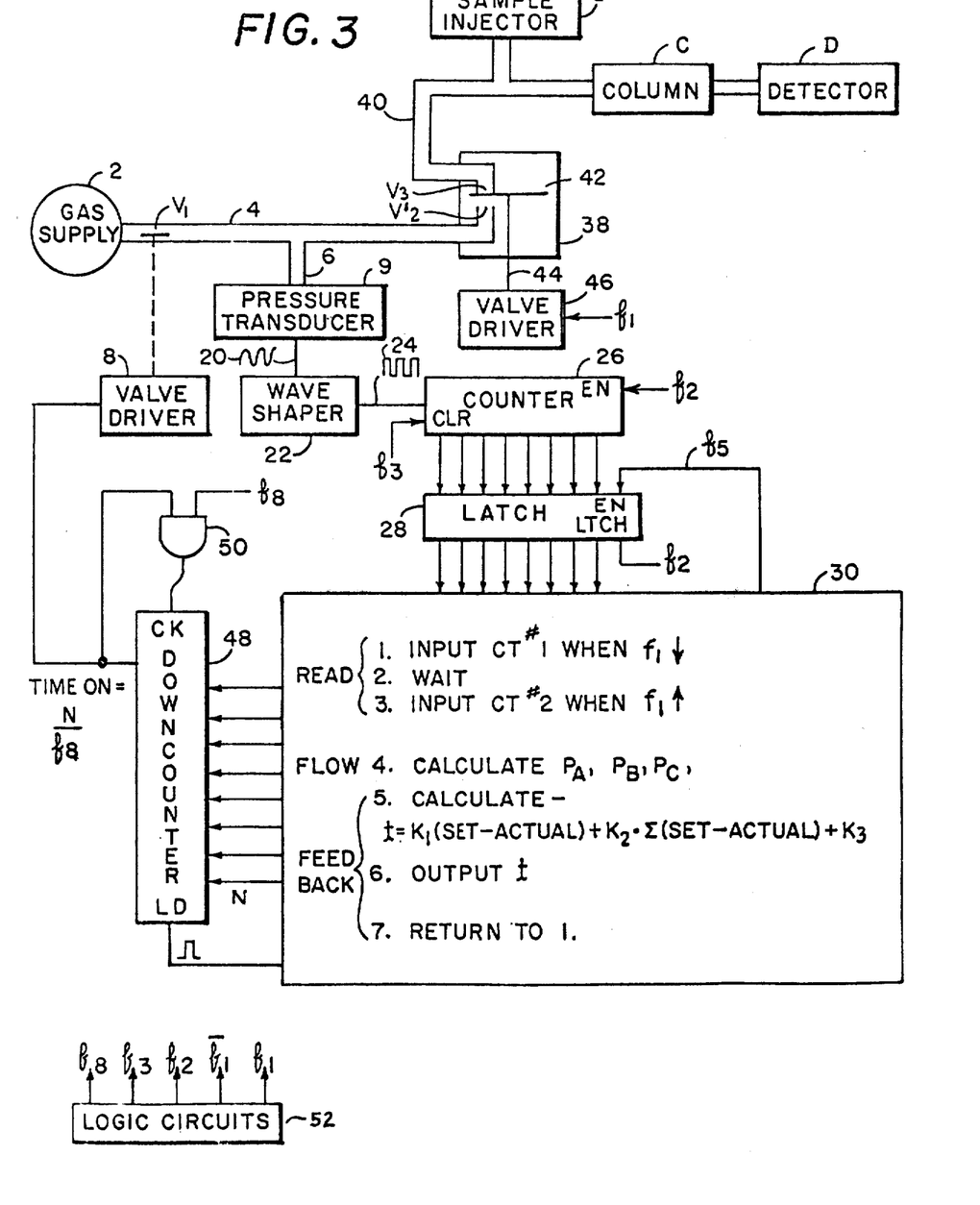
FIG. 3 illustrates apparatus incorporating the invention in such manner as to permit the pressure measurements to be made of a constant volume as in the apparatus of FIG. 2, but in which the gas flows from the volume to the load via a reference volume.

Reference is now made to the embodiment of the invention illustrated in FIG. 3, wherein components corresponding to the other embodiments are designated by the same numerals. It is to be noted that the regulator valve $V_R$ has been eliminated so that the pressurized gas supply 2 is directly connected to the tube 4, and that instead of connecting the tube 4 directly to a load such as the chromatographic column C, it is connected to a load via a three-way valve. The latter is comprised of a tank 38 into which the end of the tube 4 that is remote from the gas supply 2 is inserted. One end of a tube 40 is inserted into the tank 38, and its other end is connected to the load, herein shown as the column C. Right-angle elbows are formed in the ends of the tubes 4 and 40 that are within the tank 38 so that the end openings are spaced from and opposed to each other as shown. A horizontal diaphragm 42 is mounted on the end of a rod 44 that is actuated up and down by a valve drive 46 under the control of a voltage wave $f_1$ illustrated in FIG. 3A. The diaphragm 42 and the end of the tube 4 constitute a valve $V_2'$, and the diaphragm 42 and the end of the tube 40 constitute a valve $V_3$. When the diaphragm 42 is in its upper position, as shown, it closes off the end of the tube 40 but permits gas to flow through the tube 4 into the tank 38. When the diaphragm 42 is in its lower position, it closes off the end of the tube 4 but permits gas to flow from the tank 38 into the tube 40 and thence into the column C. The volume within the tank will be referred to as the reference volume $R_V$.

If the computer, indicated by the rectangle 30, is an HP Model 21 MX computer, it can be made to perform the READ, FLOW and FEEDBACK functions indicated within the rectangle 30 by the programs indicated by these titles at the end of the specification. These functions are performed under the direction of a MAIN PROGRAM, also included at the end of the specification. After the counts Ct#1 and Ct#2 (see FIG. 3A) that are respectively made during quarter-cycles $Q_2$ and $Q_4$ are received, the processor 30 calculates the pressures $P_A$ and $P_B$ in accordance with the following equations in order to take into account the characteristics of the pressure transducer 9.

$$P_A = A + B(Ct\#1)^2 + C(Ct\#1)^4 \qquad (4)$$

$$P_B = A + B(Ct\#2)^2 + C(Ct\#2)^4 \qquad (5)$$

The constants A, B and C are calibration constants specific to the particular transducer. They may vary from transducer to transducer, but will remain the same for a given transducer. From the true pressures $P_A$ and $P_B$, the mass flow for the time $\Delta t$ can be calculated from $$\dot{m} = \frac{V}{RT\Delta t}(P_A - P_B) \qquad (6)$$

The difference between the mass flow just calculated and the mass flow desired is used in accordance with the FEED-BACK program to generate a digital number N that increases with the difference. When this is completed, the processor 30 supplies a load pulse to the load terminal of a downcounter 48 so as to transfer the digital number N to it. The output of the downcounter 48 is high as long as the count is other than zero and is connected to one input of an AND gate 50. Square wave pulses of a high frequency $f_8$ are applied to the other input of the gate 50, and its output is connected to the clock terminal of the downcounter 48. The output of the downcounter 48 is also connected to the valve drive 8 for the valve $V_1$. The various pulse waves $\overline{f_1}$, $f_1$, $f_2$, $f_7$ and $f_8$ are generated by logic circuits 52.

Operation of FIG. 3

Figure 3A:
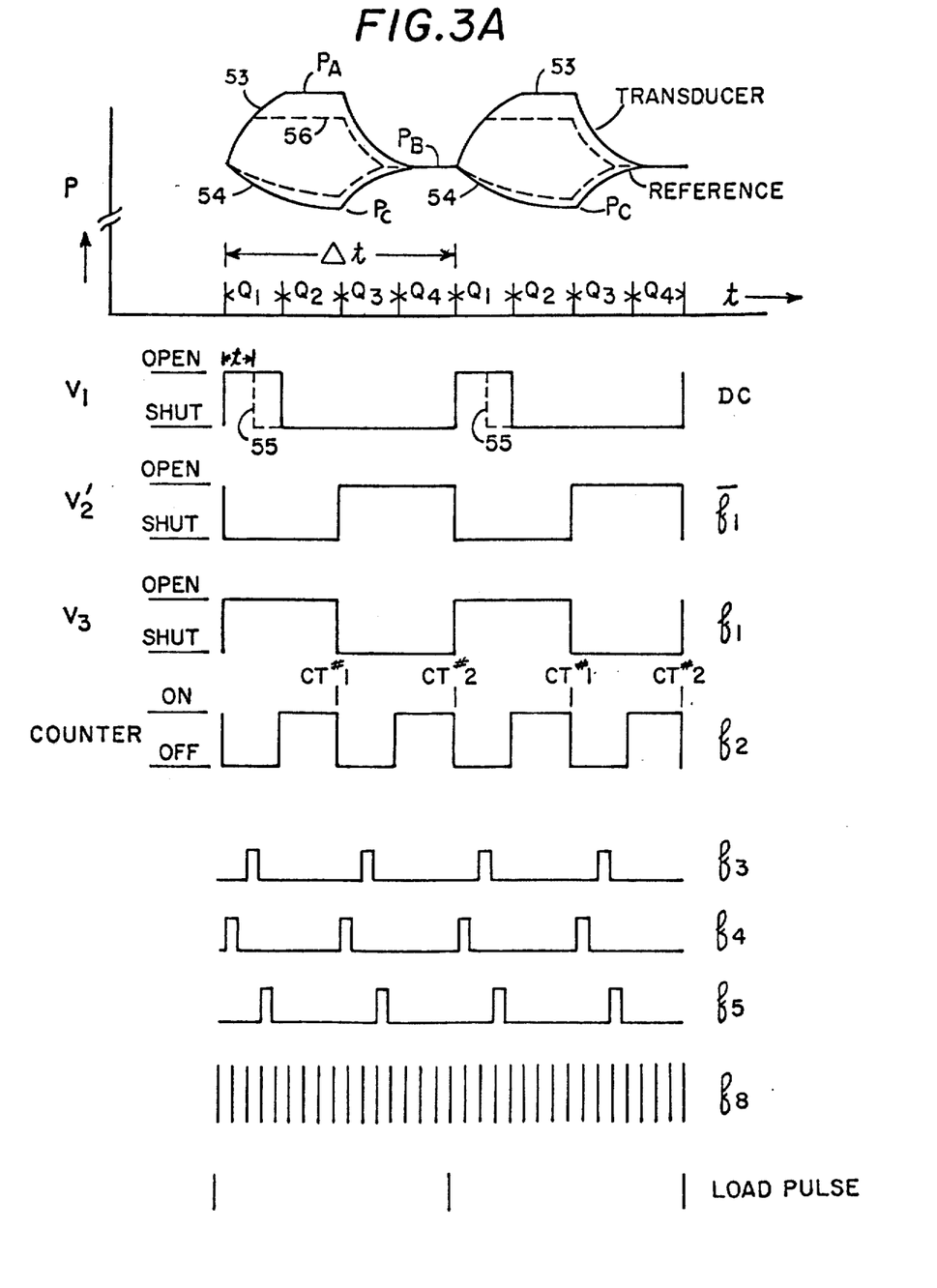

In explaining the operation of FIG. 3, reference will be made to the graphs of FIG. 3A. In the graphs P of pressure variations, the solid line graph 53 represents the variation in pressure in the volume V comprised of the pressure transducer 9, the tube 6, and the portion of the tube 4 between the valve $V_1$ and the valve $V_2'$. $V_2'$ is located in the same relative position as the valve $V_2$ of FIG. 2, but differs from it in that it controls conduction between the tube 4 and the reference volume $R_V$ of the tank 38 rather than between the tube 4 and the column C. In other words, the tube 4 is coupled to the column C via the valve $V_2'$, but indirectly through the tank 38. The reason for this will be set forth later. The solid line graph 54 represents the pressure in the reference volume $R_V$ of the tank 38.

Assuming that a maximum increase in pressure or flow is called for, the valve $V_1$ remains open for the entire first quarter $Q_1$, as indicated by the graph DC representing the output of the downcounter 48. Regardless of the variation in pressure or flow demanded, the valve $V_2'$ is closed during the quarters $Q_1$ and $Q_2$, as indicated by the graph $\overline{f_1}$. During $Q_2$, the counter 26 is activated, as shown in the graph $f_2$, so as to count the number of cycles, Ct#1, provided by the waveshaper 22 during this time. As previously explained, the processor 30 computes the pressure $P_A$ from Ct#1. Thus, as indicated by the graph 53, the pressure in the volumn V increases during the quarter $Q_1$ and holds at a steady value $P_A$ during $Q_2$ when both $V_1$ and $V_2'$ are closed. During $Q_1$ and $Q_2$, the valve $V_3$ is open so that gas flows from the reference volume $R_V$ of the tank 38 to the column C via the tube 40, thus lowering the pressure as indicated by the graph 54.

At the end of $Q_2$, $V_2'$ opens and $V_3$ closes, as indicated by the graphs $\overline{f_1}$ and $f_1$, i.e., these valves operate out of phase with each other. The valve $V_1$ remains closed so that the pressures in the volume V, associated with the transducer 9, and the reference volume $R_V$ of the tank 38 start to equilibrate. The volumes of the transducer 9 and the tank 38, as well as the hydraulic resistance of the tube 4, are such that full equilibration can occur for the maximum differential in pressure by the end of $Q_3$. Thus, as indicated by the transducer pressure graph 53, the pressure in the transducer 9 decreases, and as indicated by the graph 54, the pressure in the tank 38 increases until the pressures are equal. During the fourth quarter-cycle $Q_4$, the counter 26 is activated, as shown by the graph $f_2$, so as to provide the Ct#2 of cycles from which the pressure $P_B$ is calculated, as previously explained.

After $P_A$ and $P_B$ are determined, the processor 30 calculates the time t during which the valve $V_1$ is to be open in accordance with the following well-known proportional integral control algorithm:

$$\begin{aligned} t = &K_1 \text{ (Set flow } - \text{ actual flow)} \\ &+ K_2 \text{ (Set flow } - \text{ actual flow)} \\ &+ K_3 \end{aligned} \qquad (7)$$

wherein the constants $K_1$, $K_2$ and $K_3$ are such as to provide for optimum performance with the particular combination of mechanical components involved.

The processor 30 outputs a digital number N representing the time t during which $V_1$ is to be open. When this is done, the processor 30 provides a loading pulse to the load terminal of the downcounter 48, and the number N is transferred to the downcounter 48. As long as the number stored in the downcounter 48 is other than zero, its output remains high; and as long as this condition exists, the output of the AND gate 50 will be high during the positive pulses $f_8$. Inasmuch as the output of the AND gate 50 is connected to the clock terminal of the downcounter 48, its count is lowered for each of the pulses $f_8$. During this time, the high output of the downcounter 48 causes the valve drive 8 to keep the valve $V_1$ open. When the count in the downcounter 48 reaches zero, its output goes low and $V_1$ is closed. The maximum time that $V_1$ is to be open is one-quarter of a cycle, and the number N corresponding to this time is such that it equals the number of cycles of $f_8$ occurring during one quarter-cycle. The valve drive 32 of FIGS. 1 and 2 could incorporate a downcounter like 38, and its average output could be used to set the valve $V_R$.

If a lower flow or pressure is called for, the number N will be less so that the output of the downcounter 48 ceases to be positive at times indicated by the dashed lines 55 of the graph DC. The valve $V_1$ closes at this time, so that the pressure in the volume V associated with the transducer 9 follows the dotted line 56 in the graph P. The pressure in the volume is therefore constant for the last part of $Q_1$, as well as all of $Q_2$. In FIG. 2, the valve $V_1$ was closed only during $Q_2$ so that the pressure in volume V was constant only during this time. This was possible in FIG. 2 because flow or pressure was controlled by the supply valve $V_R$, but in FIG. 3, valve $V_1$ controls the pressure or flow in the manner described.

The reasons for providing the tank 38 with its reference volumn $R_V$ is that if the volume V associated with the transducer 9 is smaller than the reference volume $R_V$, the variation in pressure applied to the column is less, as illustrated by the fact that the peak-to-peak amplitude of the pressure wave 54 is less than the peak-to-peak amplitude of the pressure wave 53. Without the tank 38, the variation in pressure applied to the column C would be as indicated by the graph 53; but with the tank 38, the pressure applied to the column C is as indicated by the graph 54. The ratio of the peak-to-peak pressures is inverse to the ratio of the volumes. An additional advantage is that the smaller the transducer volume V, the greater is the sensitivity.

Constant Pressure Operation

It is often desired to maintain a constant predetermined pressure at the head of the column C. In the apparatus of FIGS. 1 and 2, the pressure at the head of the column is very close to the pressure, $P_B$, measured during the quarter-cycle $Q_4$, but this is not the case in the apparatus of FIG. 3 because the pressure $P_B$ is the equilibrated pressure between the effective transducer volume V and the reference volume $R_V$ of the tank 38 and has no direct relationship to the pressure at the head of the column C. The column pressure is very close to that indicated at $P_C$, which is the lowest pressure in the tank 38 when it is exhausting into the column. Once the flow rate m is known from equation (6), the pressure $P_C$ can be calculated from the following relationship:

$$P_C = P_B - \frac{\dot{m}RT}{R_V} \tag{8}$$

where T is the temperature of the reference volume in the tank 38. The difference between the actual $P_C$ thus determined and the pressure desired may be used to determine the number N that controls the time the valve $V_1$ is to be open during the first quarter-cycle $Q_1$.

Comments

In explaining the operation of the various embodiments of the invention, the various operations were referenced to quarter-cycles because this makes it easier to operate two chromatograph systems at the same time, but this is not a limitation as the relative times of events could be much different, e.g., the time during which the counts Ct#1 and Ct#2 are taken could be less than a quarter-cycle.

It will be apparent that in the embodiments of both FIGS. 1 and 2 the regulating valve $V_R$ can be eliminated and mass flow or pressure controlled by operation of $V_1$ as explained in the embodiment of FIG. 3.

```
MLP FAMILY ASSEMBLER    1.1

*  VARIABLES (REGISTERS)
        *  **********************
        *
  001B  STRBGN  EQU  27      STARTING ADDR OF STRING INFORMATION
  0041  STREND  EQU  65      LAST POSSIBLE ADDR OF STRING INFORMATION
        *
        *  EACH STRING ENTRY OCCUPIES TWO BYTES.  THE FIRST BYTE CONTAINS
        *  THE PATTERN #.  THE SECOND BYTE CONTAINS THE FUNCTIONS FOR THAT
        *  PATTERN:
        *                   BIT 0 = RIGHT OVERRIDE FLAG
        *                   BIT 1 = FEED OVERRIDE FLAG
        *                   BIT 2 = 2X FLAG
        *                   BIT 3 = MIRROR FLAG
        *                   BIT 4 = FEED MIRROR FLAG
        *                   BITS 5,6,7 UNUSED
        *
  0041  SUM1    EQU  R65     THESE SUM REGISTERS OVERLAP THE STRINGING
  0042  SUM2    EQU  R66     AREA, BUT STRINGING IS NOT ACTIVE WHILE
        *                    THEY ARE USED.
  0043  SYNCRF  EQU  R67     MACHINE SYNC REFERENCE  (INDICATES SPEED)
        *
  0044  FLAGS   EQU  R68
  0044  SYNC    EQU  R68     1=RIGHT,0=FEED
  0045  BCTK    EQU  R69     BACKTACK FLAG  0=OFF,1=INSTANTANEOUS,B0=SUSTAI
  0046  SP      EQU  R70     SINGLE PATTERN FLAG
  0047  BUTT    EQU  R71     BUTTONHOLE FLAG
  0048  MIRROR  EQU  R72     MIRROR FLAG
  0049  MIRFED  EQU  R73     FEED MIRROR FLAG
  004A  TWOX    EQU  R74     TWOX FLAG: 0=OFF,1=ON,B1=TWOX  ACTIVE
        *
  004B  STNO    EQU  R75     STITCH NUMBER
  004C  DATASP  EQU  R76     DATA STEPPING FLAG : 1=ACTIVE,0=OFF
  004D  SPARK   EQU  R77     SPARK ADVANCE FLAG
  004E  EOP     EQU  R78     END OF PATTERN FLAG:0=OFF,1=ON,B1=SPEOP
  004F  CNPAT   EQU  R79     CENTER NEEDLE ONLY PATTERNS
  0050  RZZF    EQU  R80     RIGHT ZIG-ZAG FLAG  0=OFF,1=ON
  0051  SWITCH  EQU  R81     BUTTONHOLE SWITCH FLAG
  0052  BAL     EQU  R82     BALANCE FLAG
        *
  0053  INTCNT  EQU  R83     INTERRUPT COUNTER
  0054  ICNT1   EQU  R84     INTERRUPT COUNTER 1
  0055  PATNO   EQU  R85     PATTERN NUMBER
  0056  PPATNO  EQU  R86     PREVIOUS PATTERN NUMBER
  0057  BHST    EQU  R87     STITCH COUNTER USED BY BUTTONHOLE
        *                    (BH CONTACT IGNORED UNLESS COUNT=0)
        *
  0058  MIRTMP  EQU  R88     TEMP LOC USED BY FEED MIRROR
  0059  NEWPAT  EQU  R89     INDICATES NEW PATTERN IF SET
  005A  LEDTMP  EQU  R90     TEMP LED DATA HOLDER
```

```
0181    005B    BREG    EQU     R91             VALUE OF BIGHT AT OUTPUT
0182    005C    BREG1   EQU     R92             DESIRED BIGHT VALUE
0183    005D    FREG    EQU     R93             VALUE OF FEED AT OUTPUT
0184    005E    FREG1   EQU     R94             DESIRED FEED VALUE
0185    005F    FREG2   EQU     R95             NEW FEED DATA (ISN'T PUT INTO FREG1 UNTIL
0186                                             FEED SYNC)
0187            *
0188    0060    RPCNT   EQU     R96             BEEPER COUNTER
0189    0061    PSL     EQU     R97             REGISTER TO STORE LAST FEED DURING REV
0190            *
0191    0062    RECYC   EQU     R98             RECYCLE FLAG
0192    0063    MEND    EQU     R99             MENDING FLAGS  BIT 1=PREVIOUS MENDING FLAG
0193                                                            BIT 0=CURRENT MENDING FLAG
0194            *
0195    0064    IABUFM  EQU     R100            INDIRECT ADDR BUFFER (MS BYTE)
0196    0065    IABUFL  EQU     R101                                 (LS BYTE)
0197            *
0198    0066    PORTE2  EQU     R102            DATA ON PORT E (NEEDED SINCE E CAN'T
0199                                             BE READ)
0200    0067    PORTG2  EQU     R103            DATA ON PORT G (NEEDED SINCE G CAN'T
0201                                             BE READ)
0202            *
0203            *
0204    0068    LEDCNT  EQU     R104            LED COLUMN COUNTER
0205    0069    MACF    EQU     R105            MACHINE SYNC FLAG (USED TO TELL IF
0206                                             MACHINE IS RUNNING)
0207            *
0208    006A    COLCNT  EQU     R106            SWITCH COLUMN COUNTER
0209    006B    ROWNUM  EQU     R107            SWITCH ROW #
0210    006C    BOV     EQU     R108            BIGHT OVERRIDE FLAG
0211    006D    FOV     EQU     R109            FEED OVERRIDE FLAG
0212    006E    FFCODE  EQU     R110            FORCED FEED CODE
0213    006F    TOUCH   EQU     R111            PANEL TOUCH FLAG
0214            *
0215    0070    MODULF  EQU     R112            EXTERNAL MODULE FLAG
0216            *
0217    0071    IABFM2  EQU     R113            INDIRECT ADDR BUFF FOR STRINGING (MS BYTE)
0218    0072    IABFL2  EQU     R114                                             (LS BYTE)
0219            *
0220    0073    TBMIL   EQU     R115            COUNTER WHICH IS DEC EVERY 8 MILLISECONDS
0221            *
0222    0074    STRPTR  EQU     R116            POINTER TO CURRENT ENTRY IN STRING
0223    0075    STRFIN  EQU     R117            POINTER TO NEXT FREE PLACE IN STRING
0224    0076    STRFLG  EQU     R118            STRINGING FLAGS:
0225
0226            * ----------------------------------------
0227            * !     !     !     !     !     !     !     !     !
0228            * !     !     !     !     !     !     !     !     !
0229            * ----------------------------------------
0230            *
0231            *                                               !-MRC! 1=ON
0232            *                                               !-UPDATE LEDS?! 1=YES
0233            *                                         !-STITCHES SEWN?! 1=NO, 0=YES
0234            *                                   !-- CLR FLAG! 1= CLEAR PRESSED ONCE
0235            *                             !-- BLINK MRC LED ?! 1=YES, 0=OFF
0236            *                       !-- MRC LED FLAG! 1=ON, 0=OFF
0237            *                 !-- BLINK ENTER LED ?! 1=YES, 0=NO
0238            *           !-- ENTER LED FLAG! 1=ON, 0=OFF
0239
0240            *
0241    0077    SPEED   EQU     R119            MOTOR SPEED (PERIOD)
0242
0243    0078    COLADR  EQU     120
0244    0078    COL0    EQU     R120
0245    0079    COL1    EQU     R121            ROW DATA FOR SPECIFIED COLUMN
0246    007A    COL2    EQU     R122
0247    007B    COL3    EQU     R123
0248    007C    COL4    EQU     R124
0249    007D    COL5    EQU     R125
0250    007E    COL6    EQU     R126
0251    007F    COL7    EQU     R127
0252
0527            *
0528            * CLEAR FUNCTION
0529            * ***************
0530            *
0531
0532
0533    00FB    77    CLEAR    BTJZ    *>01,STRFLG,NOBAL   ONLY LOOK AT CLEAR WHEN MRC ACTIVE
        00FC    01
        00FD    76
        00FE    CB
0534    00FF    72             MOV     *>BF,RPCNT
        0100    BF
        0101    60
0535    0102    76             BTJO    *>08,STRFLG,CLEAR1  IS CLR BIT SET ?
        0103    08
        0104    76
        0105    05
0536            *
0537            * BIT IS NOT SET (CLEAR HAS NOT BEEN PUSHED)
0538            *
0539    0106    74             OR      *>08,STRFLG         SET CLR BIT
        0107    08
        0108    76
0540    0109    F0             JMP     NOBAL
        010A    BF
0541            *
0542            * BIT IS SET (CLEAR HAS ALREADY BEEN PUSHED ONCE)
0543            *
0544    010B    06    CLEAR1   DINT
0545    010C    72             MOV     #STRBGN,STRPTR
        010D    1B
        010E    74
0546    010F    72             MOV     #STRBGN,STRFIN      RESET POINTERS
        0110    1B
        0111    75
```

```
0547
0548      *  MRC IS ACTIVE AND STRING HAS BEEN CLEARED.  PUT MACHINE INTO
0549      *  STRAIGHT STITCH AND BLINK MRC LED.
0550      *
0551  0112  72        MOV    %>30,STRFLG        SET MRC BLINK (STRING IS EMPTY)
      0113  30
      0114  76
0552  0115  72        MOV    #1,MACF
      0116  01
      0117  69
0553  0118  72        MOV    %HAFSEC,TBMIL
      0119  3E
      011A  73
0554  011B  05        CLR    PATNO              SET FOR STRAIGHT STITCH
      011C  55
0555  011D  77        RTJZ   %>01,MODULE,CLEAR2
      011E  01
      011F  70
      0120  03
0556  0121  BE        CALL   @FXTST1            SET PATNO TO MODULE DEFAULT PATNO
      0122  A015
0557  0124  EF   CLEAR2 TRAP PTSTUF             SET FLAGS FOR THE PATTERN
0558  0125  EA        TRAP   LEDOUT             TURN OFF ALL LEDS
0559  0126  32        MOV    PATNO,B
      0127  55
0560  0128  77        RTJZ   %>01,MODULE,CLEAR3
      0129  01
      012A  70
      012B  03
0561  012C  BE        CALL   @EXTLED            SET B TO LED # FOR PATNO IN MODULE
      012D  A009
0562  012F  E8   CLEAR3 TRAP LEDON              TURN ON PATTERN LED
0563  0130  52        MOV    %MFMSW,B
      0131  20
0564  0132  E8        TRAP   LEDON              TURN ON MRC (IT WILL BLINK)
0565  0133  F0        JMP    NORAL
      0134  95
0567
0568      *
0569      *  ENTER FUNCTION
0570      *  **************
0571      *
0572
0573  0135  76   ENTER RTJO   %>01,STRFLG,NORAL  IGNORE, MRC ACTIVE
      0136  01
      0137  76
      0138  91
0574  0139  76        RTJO   %>01,MODULE,FNTCHK
      013A  01
      013B  70
      013C  05
0575  013D  7D        CMP    #12,PATNO
      013E  0C
      013F  55
0576  0140  E2        JEQ    NORAL              IGNORE IF BARTACK
      0141  8B
0577  0142  76   FNTCHK RTJO  %>01,BUTT,NORAL    IGNORE IF BUTTONHOLE
      0143  01
      0144  47
      0145  84
0578  0146  76        RTJO   %>01,MEND,NORAL    IGNORE IF MENDING
      0147  01
      0148  63
      0149  80
0579      *
0580  014A  7D        CMP    %STREND,STRFIN
      014B  41
      014C  75
0581  014D  E2        JEQ    ENTOK              THERE IS ROOM FOR ENTRY
      014E  15
0582  014F  F7        JNC    FNTOK              THERE IS ROOM FOR ENTRY
      0150  13
0583  0151  76        RTJO   %>08,STRFLG,ENTOK  NO ROOM, BUT ITS REPLACEMENT SO OK
      0152  08
      0153  76
      0154  0F
0584      *
0585      *  NO ROOM! BLINK ENTER
0586      *
0587  0155  52        MOV    %ENTSW,B
      0156  1F
0588  0157  E8        TRAP   LEDON
0589  0158  74        OR     %>C0,STRFLG        SET BLINK BITS
      0159  C0
      015A  76
0590  015B  72        MOV    %HAFSEC,TBMIL
      015C  3E
      015D  73
0591  015E  72        MOV    #1,MACF
      015F  01
      0160  69
0592  0161  BC        BR     @PNPEEK
      0162  0045*
0593      *
0594      *  THERE IS ROOM! INSERT ENTRY
0595      *
0596  0164  72   FNTOK MOV   %>BF,BPCNT         SET BEEPER
      0165  BF
      0166  60
0597  0167  52        MOV    %MFMSW,B
      0168  20
0598  0169  E9        TRAP   LEDOFF             MAKE SURE MRC IS OFF (MAY HAVE
0599      *                                     BEEN BLINKING)
0600  016A  52        MOV    %ENTSW,B
      016B  1F
0601  016C  E9        TRAP   LEDOFF             MAKE SURE ENTER IS OFF
0602  016D  73        AND    %>0F,STRFLG
```

```
        016E  0F
        016F  76
0603    0170  76          RTJO    %>08,STRFLG,ENTREP
        0171  0A
        0172  76
        0173  30
0604                *
0605    0174  42   FNTSET MOV     STRFIN,STRPTR
        0175  75
        0176  74
0606    0177  78          ADD     %2,STRFIN           BUMP POINTER
        0178  02
        0179  75
0607                *
0608    017A  42   FNTPUT MOV     STRPTR,IABFL2
        017B  74
        017C  72
0609    017D  D5          CLR     IABFM2
        017E  71
0610    017F  12          MOV     PATNO,A
        0180  55
0611    0181  9B          STA     *IABFL2             SAVE PATTERN #
        0182  72
0612    0183  12          MOV     BOV,A
        0184  6C
0613    0185  77          RTJZ    %>01,FOV,ENTST1     PACK FUNCTION FLAGS INTO A
        0186  01
        0187  6D
        0188  02
0614    0189  24          OR      %>02,A
        018A  02
0615    018B  32   FNTST1 MOV     TWOX,B
        018C  4A
0616    018D  E2          JEQ     FNTST2
        018E  02
0617    018F  24          OR      %>04,A
        0190  04
0618    0191  77   FNTST2 RTJZ    %>01,MIRROR,ENTST3
        0192  01
        0193  4B
        0194  02
0619    0195  24          OR      %>08,A
        0196  08
0620    0197  77   FNTST3 RTJZ    %>01,MIRFED,FNTST4
        0198  01
        0199  49
        019A  02
0621    019B  24          OR      %>10,A
        019C  10
0622    019D  03   FNTST4 INC     IABFL2
        019E  72
0623    019F  9B          STA     *IABFL2             SAVE FUNCTIONS
        01A0  72
0624    01A1  8C          BR      @PNPEEK
        01A2  0045
0625                *
0626                *
0627    01A4  73   FNTREP AND     %>F7,STRFLG         CLEAR CLR BIT
        01A5  F7
        01A6  76
0628    01A7  70          CMP     *STRBGN,STRFIN
        01A8  1B
        01A9  75
0629    01AA  F2          JEQ     FNTSET              STRING IS EMPTY, CAN'T REPLACE
        01AB  CA
0630    01AC  E0          JMP     FNTPUT              REPLACE CURRENT ENTRY
        01AD  CC
0632                *
0633                *   MEMORY RECALL ROUTINE
0634                *   ************************
0635                *
0636
0637    01AE  73   MEMORY AND     %>F7,STRFLG         SHUT OFF CLR BIT
        01AF  F7
        01B0  76
0638    01B1  70          CMP     *STRBGN,STRFIN      IS THE STRING EMPTY ?
        01B2  1B
        01B3  75
0639    01B4  E2          JEQ     MEMNO               YES
        01B5  3F
0640                *
0641                *   STRING IS NOT EMPTY. SET BEEPER & POINTER TO APPROPRIATE VALUE
0642                *
0643    01B6  72          MOV     %>BF,BPCNT          SET BEEPER
        01B7  BF
        01B8  60
0644    01B9  76          RTJO    %>01,STRFLG,MRCSET  IS MRC BIT ALREADY SET ?
        01BA  01
        01BB  76
        01BC  06
0645
0646    01BD  06   MEMST  DINT
0647    01BE  72   MEMST1 MOV     *STRBGN,STRPTR      POINT TO BEGINNING OF STRING
        01BF  1B
        01C0  74
0648    01C1  E0          JMP     MRCRTN              SET UP FOR PATTERN POINTED TO
        01C2  0D
0649
0650    01C3  77   MRCSET RTJZ    %>04,STRFLG,MEMST   SOME OF STRING HAS BEEN SEWN,
        01C4  04
        01C5  76
        01C6  F6
0651                                                   START OVER FROM BEGINNING.
0652                *
0653                *  STRING HAS NOT BEEN SEWN, DISPLAY NEXT PATTERN
0654                *
0655    01C7  06          DINT
```

```
0656  01C8  78        ADD    #2,STRPTR            BUMP POINTER
      01C9  02
      01CA  74
0657  01CB  40        CMP    STRFIN,STRPTR        PAST END OF STRING ?
      01CC  75
      01CD  74
0658  01CE  E2        JEQ    MFMST1               YES, START OVER FROM BEGINNING
      01CF  FF
0659                  *
0660                  * SET UP FOR SEWING OR DISPLAYING PATTERN STRING
0661                  *
0662  01D0  74        MRCRTN OR    #>05,STRFLG     SET MRC BIT & SET STITCHES SEWN BIT
      01D1  05
      01D2  76
0663                  *                            TO INDICATE NO STITCHES SEWN YET.
0664  01D3  D5        CLR    RCTR
      01D4  45
0665  01D5  D5        CLR    SP
      01D6  46
0666  01D7  D5        CLR    BUTT
      01D8  47
0667  01D9  D5        CLR    SWITCH
      01DA  51
0668  01DB  D5        CLR    MEND
      01DC  63
0669  01DD  ED        TRAP   MFMPAT
0670  01DE  05        FINT
0671  01DF  06        DINT                         (ALLOW TIMER INT IF IT HAS BEEN WAITING)
0672  01E0  32        MOV    PORTG2,R             ENABLE DRIVE MOTOR IF NECESSARY
      01E1  67
0673  01E2  53        AND    #>07,R
      01E3  07
0674  01E4  E6        JNE    ENINT?
      01E5  08
0675  01E6  74        OR     #MTR700,PORTG2       MOTOR WAS SHUT OFF (VALUE=0)
      01E7  04
      01E8  67
0676  01E9  12        MOV    PORTG2,A
      01EA  67
0677  01EB  BB        STA    @PORTG
      01EC  0000
0678  01EE  05        ENINT? FINT
0679  01EF  73        AND    #>0F,STRFLG          MAKE SURE LEDS DON'T BLINK
      01F0  0F
      01F1  76
0680  01F2  8C        MEMFIN BR    @PNPEEK
      01F3  0045
0681                  *
0682                  * STRING IS EMPTY.  BLINK MRC
0683                  *
0684  01F5  52        MEMNO  MOV   #MEMSW,R
      01F6  20
0685  01F7  E8        TRAP   LEDON
0686  01F8  74        OR     #>30,STRFLG          BLINK MRC
      01F9  30
      01FA  76
0687  01FB  72        MOV    #HAFSEC,TBMIL        SET 1/2 SECOND TIMER
      01FC  3E
      01FD  73
0688  01FE  72        MOV    #1,MACE
      01FF  01
      0200  69
0689  0201  E0        JMP    MEMFIN
      0202  EF
```

What is claimed is:

1. Apparatus for controlling the flow of a gas from a pressurized source so as to maintain a constant mass flow to a load, comprising a valve having an input to which gas under pressure may be coupled and an output, means defining a volume V having an inlet port coupled to the output of said valve and an outlet port to which a load may be coupled, pressure signal producing means including a transducer for producing, when activated, an electrical signal representing the pressure in said volume V, means for placing said valve in an open position during a first portion of each of a plurality of successive cycles and for placing it in a closed position during the remainder of each cycle, each cycle having a duration $\Delta t$, means for activating said pressure signal producing means during the end of said first portion of each cycle so as to produce a signal representing the pressure $P_A$ of the gas in the volume V, means for activating said pressure signal producing means during the end portion of each cycle so as to produce a signal representing the pressure $P_B$ of the gas in the volume V, means responsive to the signals representing the pressures $P_A$ and $P_B$ for each cycle for deriving a control signal representing the mass flow m through the volume V equal to $$\frac{P_A - P_B}{\Delta t} \cdot \frac{V}{RT}$$

wherein R is the universal gas constant and T is the absolute temperature of the gas in the volume V, and control means responsive to said control signal for controlling the amount of gas that flows through said valve in each cycle so as to maintain the mass flow m at a predetermined set value.

2. Apparatus for controlling the flow of gas so as to maintain a constant mass flow to a load, comprising a first valve having an input to which gas under pressure may be coupled and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, each cycle having a duration of Δt, a second valve having an input coupled to the outlet port of said volume and an output to which a load can be coupled, means for placing said second valve in a closed position during said first portion of each cycle and during a second portion of said cycle occurring immediately after said first valve is closed and for placing said second valve in an open position during the remainder of the cycle, means for activating said pressure signal producing means during said second portion of each cycle so as to produce a signal $P_A$ representing the pressure in said volume V and for activating said pressure signal producing means during the last portion of each cycle so as to produce a signal $P_B$ representing the pressure in said volume V, means responsive to the signals representing $P_A$ and $P_B$ for deriving a control signal representing the mass flow ṁ through the volume V equal to $$\frac{P_A - P_B}{\Delta t} \cdot \frac{V}{RT}$$

wherein R is the universal gas constant and T is the temperature of the gas in the volume V, and control means responsive to said control signal for controlling the amount of gas that flows through said first valve in each cycle so as to maintain the mass flow ṁ at a predetermined set value.

3. Apparatus for controlling the flow of gas so as to maintain a constant pressure in a load, comprising a first valve having an input to which gas under pressure may be coupled and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, each cycle having a duration Δt, a second valve having an input coupled to the outlet port of said volume and an output to which a load can be coupled, means for placing said second valve in a closed position during said first protion of a cycle, during a second portion of a cycle immediately thereafter, and during a last portion of each cycle and placing said second valve in an open position between said second and last portions of said cycle, means for activating said pressure signal producing means during one of the second and last portions of each cycle so as to produce a signal $P_A$ or a signal $P_B$ respectively representing the maximum and minimum pressures in the volume V while said first and second valves are closed, and control means responsive to the pressure signal produced by said signal producing means for controlling the flow amount of gas that flows through said first valve in each cycle so as to maintain the corresponding pressure at a predetermined set value.

4. Apparatus for controlling the flow of gas from a pressurized source to a load so as to cause a constant mass flow therein, comprising a first valve having an input to which gas under pressure may be coupled and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, each cycle having a duration Δt, a second valve having an input coupled to the outlet port of said volume and an output to which a load can be coupled, means for placing said second valve in a closed position during said first portion of a cycle, during a second portion of a cycle occurring immediately thereafter, and during a last portion of each cycle and placing it in an open position in between said second and last portions of said cycle, means for activating said pressure signal producing means during said second portion of each cycle so as to produce a signal $P_A$ representing the pressure in said volume V with said first and second valves closed, means for activating said pressure signal producing means during said last portion of each cycle so as to produce a signal $P_B$ representing the pressure in said volume V with said first and second valves closed, means responsive to the signals $P_A$ and $P_B$ for deriving a control signal representing the mass flow ṁ through the volume V equal to $$\frac{P_A - P_B}{\Delta t} \cdot \frac{V}{RT}$$

wherein R is the universal gas constant and T is the temperature of the gas in the volume V, and control means responsive to said control signal for controlling the amount of gas that flows through said first valve in each cycle so as to maintain the mass flow m at a predetermined set value.

5. Apparatus for controlling the flow of a gas so as to maintain a constant mass flow to a load, comprising a first valve having an input to which gas under pressure may be coupled and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, each cycle having a duration $\Delta t$, means defining a reference volume $R_V$, a second valve having an input coupled to the outlet port of said volume and an output coupled to said reference volume $R_V$, means placing said second valve in a closed position during the said first portion of each cycle and for a second portion occurring immediately thereafter and placing said second valve in an open position during the remainder of each cycle, a third valve having an input coupled to said reference volume $R_V$ and an output to which a load can be coupled, means for placing said third valve in an open position when said second valve is closed and placing said third valve in a closed position when said second valve is open, means activating said pressure signal producing means during the second portion of each cycle so as to produce a signal representing the pressure $P_A$ in said volume V when said first and second valves are closed, means activating said pressure signal producing means during the last portion of each cycle so as to produce a signal representing the pressure $P_B$ in said volume V and said volume $R_V$ when said first and third valves are closed, means responsive to the signals $P_A$ and $P_B$ for deriving a control signal representing the mass flow $\dot{m}$ through the volume V equal to $$\frac{P_A - P_B}{\Delta t} \cdot \frac{V}{RT}$$

wherein R is the universal gas constant and T is the temperature of the gas in the volume V, and control means responsive to said control signal for controlling the amount of gas that flows through said first valve in each cycle so as to maintain the mass flow $\dot{m}$ at a predetermined set value.

6. Apparatus for controlling the flow of a gas so as to maintain a constant pressure on a load, comprising a first valve having an input to which gas under pressure may be coupled and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, each cycle having a duration $\Delta t$, means defining a reference volume $R_V$.

a second valve having an input coupled to the outlet port of said volume V and an output coupled to said reference volume $R_V$, means placing said second valve in a closed position during the said first portion of each cycle and for a second portion occurring immediately thereafter and placing it in an open position during the remainder of each cycle, a third valve having an input coupled to said reference volume $R_V$ and an output to which a load can be coupled, means placing said third valve in an open position when said second valve is closed and placing it in a closed position when said second valve is open, means activating said pressure signal producing means during the second portion of each cycle so as to produce a signal representing the pressure $P_A$ in said volume V when said first and second valves are closed, means activating said pressure signal producing means during the last portion of each cycle so as to produce a signal representing the pressure $P_B$ in said volumes V and $R_V$ when said first and third valves are closed, and means coupled to said signal producing means for controlling the amount of gas that flows through said first valve in each cycle so as to keep a pressure $P_C$ in said reference volume equal to a predetermined set pressure, the pressure $P_C$ being equal to $$P_B - \frac{\dot{m}RT}{R_V}$$

wherein $\dot{m}$ equals $$\frac{P_A - P_B}{\Delta t} \cdot \frac{V}{RT},$$

R is the universal gas constant and T is the absolute temperature.

7. Apparatus for controlling the flow of gas so as to maintain a constant pressure in a load, comprising a first valve having an input to which gas under pressure may be coupled and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, a second valve having an input coupled to the outlet port of said volume and an output, means for placing said second valve in a closed position during said first portion of each cycle and a second portion of each cycle occurring immediately after said first valve is closed and for placing said second valve in an open position during the remainder of the cycle, means for activating said pressure signal producing means during said second portion of each cycle so as to produce a signal $P_A$ representing the pressure in said volume V and for activating said pressure signal producing means during a last portion of each cycle so as to produce a signal $P_B$ representing the pressure in said volume V, and control means responsive to one of the signals $P_A$ or $P_B$ for controlling the amount of gas that flows through said first valve in each cycle so as to maintain it at a predetermined set value.

8. Apparatus as set forth in claim 7 wherein said control means maintains the pressure $P_B$ at a predetermined value.

9. Apparatus for controlling the flow of a gas so as to maintain a constant pressure on a load, comprising
a first valve having an input to which gas under pressure may be coupled and an output,
means defining a volume V having an inlet port coupled to the output of said first valve and an outlet port,
pressure signal producing means including a transducer for producing, when activated, an electrical signal representing the pressure in said volume V,
means for placing said first valve in an open position during a first portion of each of a plurality of successive cycles and for placing it in a closed position during the remainder of each cycle,
means defining a reference volume $R_V$,
a second valve having an input coupled to the outlet port of said volume and an output coupled to said reference volume $R_V$,
means placing said second valve in a closed position during the said first portion of each cycle and for a second portion occurring immediately thereafter and placing said second valve in an open position during the remainder of each cycle,
a third valve having an input coupled to said reference volume $R_V$ and an output to which a load can be coupled,
means for placing said third valve in an open position when said second valve is closed and placing said third valve in a closed position when said second valve is open,
means activating said pressure signal producing means during the second portion of each cycle or the last portion of each cycle, and
control means responsive to the signal produced in each cycle by said pressure signal producing means for controlling the amount of gas that flows through said first valve in each cycle so as to maintain the pressure which the signal from said pressure signal producing means represents at a predetermined set value.

10. Apparatus as set forth in claim 9 wherein said means for activating said pressure signal producing means activates it only during the last portion of each cycle, and
said control means responds to the signal produced by said pressure signal producing means at the last portion of each cycle to control the flow of gas through said first valve so as to maintain the said pressure at a predetermined set value.

11. Apparatus for controlling the flow of a gas from a pressurized source so as to maintain a constant pressure on a load, comprising
a valve having an input to which gas under pressure may be coupled and an output,
means defining a volume V having an inlet port coupled to the output of said valve and an outlet port to which a load may be coupled,
pressure signal producing means including a transducer for producing, when activated, an electrical signal representing the pressure in said volume V,
means for placing said valve in an open position during a first portion of each of a plurality of successive cycles and for placing it in a closed position during the remainder of each cycle,
means for activating said pressure signal producing means during the end of said first portion of each cycle so as to produce a signal representing the pressure $P_A$ of the gas in the volume V,
means for activating said pressure signal producing means during the end portion of each cycle so as to produce a signal representing the pressure $P_B$ of the gas in the volume V, and
means responsive to one of the signals representing the pressures $P_A$ or $P_B$ for controlling the amount of gas that flows through said valve in each cycle so as to maintain said one pressure at a predetermined set value.

12. Apparatus for controlling the flow of a gas from a pressurized source so as to maintain a constant pressure on a load, comprising
a valve having an input to which gas under pressure may be coupled and an output,
means defining a volume V having an inlet port coupled to the output of said valve and an outlet port to which a load may be coupled,
pressure signal producing means including a transducer for producing, when activated, an electrical signal representing the pressure in said volume V,
means for placing said valve in an open position during a first portion of each of a plurality of successive cycles and for placing it in a closed position during the remainder of each cycle,
means for activating said pressure signal producing means during one of the end of said first portion of each cycle and the end portion of each cycle so as to respectively produce a signal $P_A$, representing the maximum pressure of the gas in the volume V, or a signal $P_B$, representing the minimum pressure of the gas in the volume V, and
control means responsive to the signals produced by said signal producing means for controlling the amount of gas that flows through said valve in each cycle so as to maintain the corresponding pressure at a predetermined set value.

13. Apparatus for controlling the flow of gas so as to maintain a constant pressure on a load, comprising
a first valve having an input to which gas under pressure may be coupled and an output,
means defining a volume V having an inlet port coupled to the output of said first valve and an outlet port,
pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, a second valve having an input coupled to the outlet port of said volume and an output to which a load can be coupled, means for placing said second valve in a closed position during said first portion of each cycle and during a second portion of said cycle occurring immediately after said first valve is closed and for placing said second valve in an open position during the remainder of the cycle, means for activating said pressure signal producing means during one of said second portion of each cycle and said last portion of each cycle so as to produce one of pressure signals $P_A$ and $P_B$, $P_A$ representing the maximum pressure in said volume V and $P_B$ representing the minimum pressure in said volume V, and control means responsive to one of said pressure signals that is produced by said pressure signal producing means for controlling the amount of gas that flows through said first valve in each cycle so as to maintain the corresponding pressure at a predetermined set value.

14. Apparatus for controlling the flow of gas from a pressurized source to a load so as to cause a constant pressure therein, comprising a first valve having an input to which gas under pressure may be coupled and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, a second valve having an input coupled to the outlet port of said volume and an output to which load can be coupled, means for placing said second valve in a closed position during said first portion of a cycle, during a second portion of a cycle occurring immediately thereafter, and during a last portion of each cycle and placing it in an open position in between said second and last portions of said cycle, means for activating said pressure signal producing means during said second portion of each cycle and said last portion of each cycle so as to produce signals $P_A$ and $P_B$, $P_A$ representing the maximum pressure in said volume V and $P_B$ representing the minimum pressure in said volume V, and control means responsive to one of said signals for controlling the amount of gas that flows through said first valve in each cycle so as to maintain the corresponding pressure at a predetermined set value.

15. Apparatus for controlling the flow of a gas so as to maintain a constant pressure on a load, comprising a first valve having an input to which gas under pressure may be coupled and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, means defining a reference volume $R_V$, a second valve having an input coupled to the outlet port of said volume and an output coupled to said reference volume $R_V$, means placing said second valve in a closed position during the said first portion of each cycle and for a second portion occurring immediately thereafter and placing said second valve in an open position during the remainder of each cycle, a third valve having an input coupled to said reference volume $R_V$ and an output to which a load can be coupled, means for placing said third valve in an open position when said second valve is closed and placing said third valve in a closed position when said second valve is open, means activating said pressure signal producing means during the second portion of each cycle and during the last portion of each cycle, and control means responsive to one of the signals produced in each cycle by said pressure signal producing means for controlling the amount of gas that flows through said first valve in each cycle so as to maintain the pressure which the signal from said pressure signal producing means represents at a predetermined set value.

16. Apparatus as set forth in any of claims 1 through 6, 7 through 10, and 11 through 15 wherein said means for controlling the amount of gas that flows in each cycle through the valve to which a pressurized source of gas can be coupled includes a linear supply valve connected to the input of said first valve.

17. Apparatus as set forth in any of claims 1 through 6, 7 through 10, and 11 through 15 wherein said means for controlling the amount of gas that flows in each cycle through the valve to which a pressurized source of gas can be coupled includes a means for controlling the duty cycle of said first valve.

* * * * *